(12) United States Patent
Saito et al.

(10) Patent No.: US 9,102,608 B2
(45) Date of Patent: Aug. 11, 2015

(54) METHOD FOR PRODUCING PENTAFLUOROSULFANYL BENZOIC ACID

(71) Applicant: UBE Industries, Ltd., Yamaguchi (JP)

(72) Inventors: Norimichi Saito, New York, NY (US); Junichi Chika, New York, NY (US)

(73) Assignee: UBE INDUSTRIES, LTD., Yamaguchi (JP)

( * ) Notice: Subject to any disclaimer, the term of this patent is extended or adjusted under 35 U.S.C. 154(b) by 0 days.

(21) Appl. No.: 14/362,779

(22) PCT Filed: Dec. 4, 2012

(86) PCT No.: PCT/JP2012/081329
§ 371 (c)(1),
(2) Date: Jun. 4, 2014

(87) PCT Pub. No.: WO2013/084860
PCT Pub. Date: Jun. 13, 2013

(65) Prior Publication Data
US 2014/0336404 A1  Nov. 13, 2014

Related U.S. Application Data

(60) Provisional application No. 61/567,474, filed on Dec. 6, 2011.

(51) Int. Cl.
| | | |
|---|---|---|
| C07C 321/00 | (2006.01) |
| C07C 51/04 | (2006.01) |
| C07C 381/00 | (2006.01) |
| C07C 63/70 | (2006.01) |

(52) U.S. Cl.
CPC .............. *C07C 51/04* (2013.01); *C07C 63/70* (2013.01); *C07C 381/00* (2013.01)

(58) Field of Classification Search
CPC ........ C07C 381/00; C07C 51/04; C07C 63/70
See application file for complete search history.

(56) References Cited

U.S. PATENT DOCUMENTS

| | | | |
|---|---|---|---|
| 7,622,500 B2 * | 11/2009 | Gibson et al. ............... 514/469 |
| 2011/0301382 A1 | 12/2011 | Umemoto et al. |

FOREIGN PATENT DOCUMENTS

| | | |
|---|---|---|
| JP | 5-32 617 A | 2/1993 |
| JP | 2004-67525 A | 3/2004 |
| JP | 2005-526138 A | 9/2005 |

(Continued)

OTHER PUBLICATIONS

International Search Report mailed Mar. 5, 2013 in PCT/JP2012/081329.

(Continued)

*Primary Examiner* — Yevegeny Valenrod
*Assistant Examiner* — Blaine G Doletski
(74) *Attorney, Agent, or Firm* — Swanson & Bratschun, L.L.C.

(57) ABSTRACT

Provided is a simple, safe, and industrially practical method for producing a pentafluorosulfanylbenzoic acid.

This method includes (A) a providing step of providing a trihalomethyl(pentafluorosulfanylbenzene) represented by general formula (1):

[Formula 1]

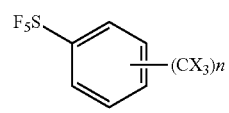

(1)

where X is a halogen atom, n is an integer of 1≤n≤3, and the hydrogen atoms on the benzene ring are optionally replaced with a group having an oxygen atom, a group having a nitrogen atom, or a halogen atom;

(B1) a step of reacting the trihalomethyl(pentafluorosulfanylbenzene) with a carboxylic acid, water, or a disiloxane represented by general formula (b):

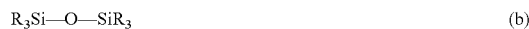

(b)

(where R is an alkyl group)
in the presence of an acid other than carboxylic acids to form a pentafluorosulfanylbenzoic halide represented by general formula (2a):

[Formula 2]

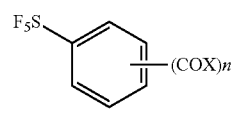

(2a)

where X and n are as defined above, and the hydrogen atoms on the benzene ring are optionally replaced with the group or atom defined above; and (B2) a step of converting the pentafluorosulfanylbenzoic halide into a pentafluorosulfanylbenzoic acid represented by general formula (2):

[Formula 3]

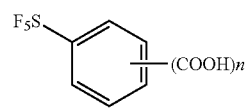

(2)

where n is as defined above, and the hydrogen atoms on the benzene ring are optionally replaced with the group or atom defined above.

9 Claims, No Drawings

(56) References Cited

FOREIGN PATENT DOCUMENTS

| JP | 2010-518067 A | 5/2010 |
|----|---------------|--------|
| WO | WO 2011/044181 A1 | 4/2011 |

OTHER PUBLICATIONS

Written Opinion mailed Mar. 5, 2013 in PCT/JP2012/081329.
International Preliminary Report on Patentability mailed Jun. 10, 2014 in PCT/JP2012/081329.

* cited by examiner

METHOD FOR PRODUCING PENTAFLUOROSULFANYL BENZOIC ACID

RELATED APPLICATIONS

This application is a 35 U.S.C. §371 national phase application of International Application Serial No. PCT/JP2012/081329, filed Dec. 4, 2012 (WO 2013/084860). International Application Serial No. PCT/JP2012/081329 claims the benefit of U.S. Provisional Application Ser. No. 61/567,474, filed Dec. 6, 2011, which is incorporated herein by reference in its entirety.

TECHNICAL FIELD

The present invention relates to methods for producing pentafluorosulfanylbenzoic acids.

BACKGROUND ART

Pentafluorosulfanylbenzoic acids are compounds useful as intermediate materials for drugs and agricultural chemicals (see, for example, PTLs 1 and 2). One known method for producing a pentafluorosulfanylbenzoic acid involves a step of reducing 4-nitro(pentafluorosulfanylbenzene) into 4-amino(pentafluorosulfanylbenzene), a step of reacting the compound with butyl nitrite to form a diazo compound and then brominating the compound with copper(II) bromide to form 4-bromo(pentafluorosulfanylbenzene), a step of lithiating the compound with t-butyllithium and then formylating the compound to form 4-(pentafluorosulfanyl)benzaldehyde, and a step of oxidizing the compound with silver oxide to form 4-(pentafluorosulfanyl)benzoic acid (NPL 1).

Another known method for producing a pentafluorosulfanylbenzoic acid involves reacting 4-bromo(pentafluorosulfanylbenzene) with metallic magnesium and methyl iodide to prepare a Grignard reagent and then reacting the reagent with carbon dioxide to form 4-(pentafluorosulfanyl)benzoic acid (NPL 2).

Still another known method involves synthesis of 4-iodo (pentafluorosulfanylbenzene) from 4-amino(pentafluorosulfanylbenzene), conversion of the compound with tributylvinyltin in the presence of a palladium catalyst into 4-vinyl (pentafluorosulfanylbenzene), and conversion of the compound with sodium periodate in the presence of a ruthenium catalyst into 4-(pentafluorosulfanyl)benzoic acid (PTL 1).

CITATION LIST

Patent Literature

PTL 1: The specification of U.S. Pat. No. 7,622,500
PTL 2: International Publication No. 2010/063767

Non Patent Literature

NPL 1: Journal of Fluorine Chemistry 2007, 128, 1449-1453.
NPL 2: Journal of the American Chemical Society 1962, 84, 3064-3072.

SUMMARY OF INVENTION

Technical Problem

The method disclosed in NPL 1 is not industrially practical for reasons such as a large number of reaction steps, inevasible synthesis of a hazardous diazo compound, and inevasible use of t-butyllithium, which is pyrophilic in air. The method disclosed in NPL 2 has disadvantages such as troublesome preparation of a Grignard reagent and low product yield. The method disclosed in PTL 1 has disadvantages such as inevasible use of an expensive catalyst and an organotin compound, which requires complicated treatment, and low product yield.

In spite of a need for industrial production of a pentafluorosulfanylbenzoic acid in a simple and safe manner, no such method has been available. In view of the foregoing background, an object of the present invention is to provide a simple, safe, and industrially practical method for producing a pentafluorosulfanylbenzoic acid, and a novel trichloromethyl(pentafluorosulfanylbenzene) suitable for use in this method of production.

Solution to Problem

The foregoing object is achieved by the following aspects:

[1] A method for producing a pentafluorosulfanylbenzoic acid includes:
(A) a providing step of providing a trihalomethyl(pentafluorosulfanylbenzene) represented by general formula (1);
(B1) a step of reacting the trihalomethyl(pentafluorosulfanylbenzene) with a carboxylic acid, water, or a disiloxane represented by general formula (b) in the presence of an acid other than carboxylic acids to form a pentafluorosulfanylbenzoic halide represented by general formula (2a); and
(B2) a step of converting the pentafluorosulfanylbenzoic halide into a pentafluorosulfanylbenzoic acid represented by general formula (2).

[2] A method for producing a pentafluorosulfanylbenzoic acid includes:
(A) a providing step of providing a trihalomethyl(pentafluorosulfanylbenzene) represented by general formula (1);
(B1) a step of reacting the trihalomethyl(pentafluorosulfanylbenzene) with a carboxylic acid, water, or a disiloxane represented by general formula (b) in the presence of an acid other than carboxylic acids to form a pentafluorosulfanylbenzoic halide represented by general formula (2a);
(C1) a step of reacting the pentafluorosulfanylbenzoic halide with an alcohol to form an ester represented by general formula (2c); and
(C2) a step of converting the pentafluorosulfanylbenzoic acid ester into a pentafluorosulfanylbenzoic acid represented by general formula (2).

Advantageous Effects of Invention

The present invention provides a simple, safe, and industrially practical method for producing a pentafluorosulfanylbenzoic acid, and a novel trichloromethyl(pentafluorosulfanylbenzene) suitable for use in this method of production.

DESCRIPTION OF EMBODIMENTS

The present invention will now be described in detail. As used herein, the term "to" indicating a numerical range is meant to encompass the values on both sides thereof.
1. Methods of Production
1-1. First Method of Production
A first method of production includes:
(A) a providing step of providing a trihalomethyl(pentafluorosulfanylbenzene) represented by general formula (1);
(B1) a step of reacting the trihalomethyl(pentafluorosulfanylbenzene) with a disiloxane represented by general formula (b), a carboxylic acid, or water in the presence of an acid other than carboxylic acids to form a pentafluorosulfanylbenzoic halide represented by general formula (2a); and (B2) a step of converting the pentafluorosulfanylbenzoic halide into a pentafluorosulfanylbenzoic acid represented by general formula (2).

The scheme of this method of production is as follows:

[Formula 1]

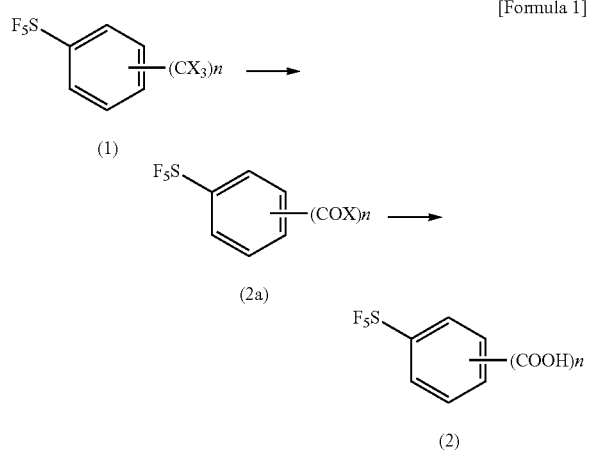

In the scheme, X is a halogen atom, and n is an integer of $1 \leq n \leq 3$. For ease of synthesis, n is preferably 1. The hydrogen atoms on the benzene ring are optionally replaced with a group having an oxygen atom, a group having a nitrogen atom, or a halogen atom. The hydrogen atoms on the benzene ring refer to the hydrogen atoms directly attached to the carbon atoms constituting the benzene ring to which the $F_5S$ group is attached.

The individual steps will now be described.

(1) Providing Step (A)

In this step, a trihalomethyl(pentafluorosulfanylbenzene) represented by general formula (1) is provided. Trihalomethyl(pentafluorosulfanylbenzene) is a generic term for compounds including a benzene ring having a pentafluorosulfanyl group and a trihalomethyl group. The benzene ring may have 1 to 3 trihalomethyl groups. The benzene ring preferably has 1 or 2 trihalomethyl groups, more preferably 1 trihalomethyl group, for ease of production because trihalomethyl groups are electron-withdrawing and a large number of such groups would cause steric hindrance. The halogen atoms on the trihalomethyl group are preferably, but not limited to, fluorine or chlorine atoms for reasons of material availability. In particular, trichloromethyl(pentafluorosulfanylbenzene)s in which the halogen atoms are chlorine atoms and n is 1 to 3 are novel substances.

The benzene ring in the trihalomethyl(pentafluorosulfanylbenzene) may be substituted by a group other than the pentafluorosulfanyl and trihalomethyl groups, although it is preferably not substituted by any other group for ease of production. Preferred examples of trihalomethyl(pentafluorosulfanylbenzene)s include monotrihalomethyl(pentafluorosulfanylbenzene)s, such as 4-trihalomethyl(pentafluorosulfanylbenzene)s and 3-trihalomethyl(pentafluorosulfanylbenzene)s; bistrihalomethyl(pentafluorosulfanylbenzene)s, such as 3,4-bistrihalomethyl(pentafluorosulfanylbenzene)s and 3,5-bistrihalomethyl(pentafluorosulfanylbenzene)s; and tristrihalomethyl(pentafluorosulfanylbenzene)s, such as 2,4,5-tristrihalomethyl(pentafluorosulfanylbenzene)s and 3,4,5-tristrihalomethyl(pentafluorosulfanylbenzene)s.

The hydrogen atoms on the benzene ring in the trihalomethyl(pentafluorosulfanylbenzene) may be replaced with a group having an oxygen atom, a group having a nitrogen atom, or a halogen atom. The halogen atom may be any halogen atom. The benzene ring may be substituted by 1 to 4 halogen atoms, which may be of two or more types.

The hydrogen atoms on the benzene ring in the trihalomethyl(pentafluorosulfanylbenzene) may be replaced with a group having an oxygen atom. Examples of such groups include hydroxy; oxocarbonylalkyl groups, such as oxocarbonylmethyl and oxocarbonylethyl; alkoxyl groups, such as methoxy, ethoxy, and benzyloxy; and aryloxyl groups, such as phenoxy and naphthoxy. The oxocarbonylalkyl groups preferably have 2 to 5 carbon atoms, more preferably 2 to 3 carbon atoms. The alkoxyl groups preferably have 1 to 10 carbon atoms, more preferably 1 to 7 carbon atoms. The aryloxyl groups preferably have 6 to 15 carbon atoms, more preferably 6 to 10 carbon atoms.

The hydrogen atoms on the benzene ring in the trihalomethyl(pentafluorosulfanylbenzene) may be replaced with a group having a nitrogen atom. Examples of such groups include primary amino groups, such as amino, monomethylamino, monoethylamino, monobenzylamino, and phenylamino; secondary amino groups, such as dimethylamino, diethylamino, dibenzylamino, methylethylamino, phenylmethylamino, and diphenylamino; primary amido and primary sulfoneamido groups, such as N-acetylamido, N-benzoylamido, and N-methanesulfonyl; and secondary amido and secondary sulfoneamido groups, such as N-methyl-N-acetoamido and N-methyl-N-methanesulfonyl. The primary amino groups preferably have 0 to 10 carbon atoms, more preferably 0 to 7 carbon atoms. The secondary amino groups preferably have 2 to 20 carbon atoms, more preferably 2 to 14 carbon atoms. The primary amido and sulfoneamido groups preferably have 1 to 10 carbon atoms, more preferably 1 to 6 carbon atoms. The secondary amido and secondary sulfoneamido groups preferably have 2 to 5 carbon atoms, more preferably 2 to 3 carbon atoms.

The benzene ring may be substituted by a total of 1 to 4 groups having an oxygen atom or a nitrogen atom.

The trihalomethyl(pentafluorosulfanylbenzene) may be provided in any manner. Preferably, the trihalomethyl(pentafluorosulfanylbenzene) is provided by reacting a methyl (pentafluorosulfanylbenzene) represented by general formula (1a) with a halogenating agent. The scheme of this reaction is as follows:

[Formula 2]

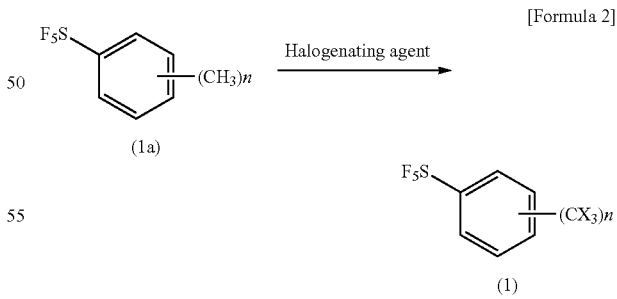

In the scheme, n is as defined above, and the hydrogen atoms on the benzene ring are optionally replaced with the group or atom defined above. X in general formula (1) is a halogen atom.

Halogenating agents are compounds that replace hydrogen with halogen. Examples of halogenating agents usable in this step include halogen molecules, such as chlorine, bromine, and iodine molecules; halogenosulfuryls, such as sulfuryl chloride, sulfuryl bromide, and sulfuryl iodide; N-halogenosuccinimides, such as N-chlorosuccinimide, N-bromosuccinimide, and N-iodosuccinimide; and 1,3-dihalogeno-5,5-dimethylhydantoins, such as 1,3-dichloro-5,5-dimethylhydantoin, 1,3-dibromo-5,5-dimethylhydantoin, and 1,3-diiodo-5,5-dimethylhydantoin. Particularly preferred are chlorine and bromine molecules, which are inexpensive, more preferably chlorine molecules.

Two or more halogenating agents having the same halogen atom may be used in combination. The halogenating agents are preferably used in an amount of 0.1 to 30 mol, more preferably 3 to 20 mol, per mole of methyl in the methyl (pentafluorosulfanylbenzene).

This reaction is preferably performed under ultraviolet irradiation. Performing the reaction under ultraviolet irradiation means that the reaction is performed while the reactants are being irradiated with natural light or a light beam containing ultraviolet light. The ultraviolet radiation generates halogen radicals, which facilitate the reaction.

This reaction requires no solvent, although a solvent that does not interfere with the reaction may be used. Examples of such solvents include inert solvents, including hydrocarbons, such as hexane and heptane, and alkyl halides, such as methylene chloride and 1,2-dichloroethane.

This reaction can be performed in the absence of a catalyst, although any catalyst may be used. Examples of catalysts, if used, include radical initiators, such as dibenzoyl peroxide and azobisisobutyronitrile; metal halides, such as aluminum chloride, aluminum bromide, aluminum iodide, zinc chloride, zinc bromide, and zinc iodide; boron halides, such as boron chloride, boron bromide, and boron iodide; and phosphorus halides, such as phosphorus trichloride, phosphorus pentachloride, phosphorus tribromide, and phosphorus pentabromide. Particularly preferred are phosphorus trichloride and phosphorus pentachloride, which are inexpensive and can facilitate the reaction. These catalysts may be used alone or in combination. The catalysts are preferably used in an amount of 0.001 to 10 mol, more preferably 0.005 to 1.0 mol, even more preferably 0.01 to 0.3 mol, per mole of the methyl (pentafluorosulfanylbenzene).

The reaction temperature for this reaction is preferably room temperature to 200° C., more preferably 40° C. to 140° C.

This reaction forms a trihalomethyl(pentafluorosulfanylbenzene) represented by general formula (1). This compound can be isolated or purified by common processes, such as neutralization, extraction, filtration, concentration, distillation, recrystallization, crystallization, sublimation, and column chromatography. X in general formula (1) is derived from the halogen atom in the halogenating agent.

(2) Step (B1)

In this step, the trihalomethyl(pentafluorosulfanylbenzene) represented by general formula (1) is reacted with a disiloxane, water, or a carboxylic acid in the presence of an acid other than carboxylic acids to form a pentafluorosulfanylbenzoic halide represented by general formula (2a). The scheme of this step is as follows:

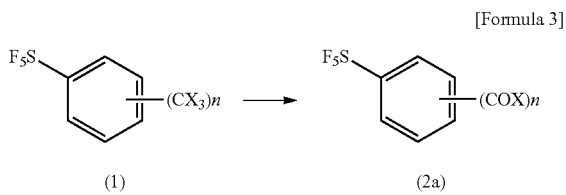

If X in general formula (1) is a fluorine atom, X in general formula (2a) is also a fluorine atom. If X in general formula (1) is a halogen atom other than fluorine atoms, X in general formula (2a) is a fluorine atom or a halogen atom other than fluorine atoms. That is, for example, if X in general formula (1) is chlorine, X in general formula (2a) is fluorine or chlorine. This fluorine atom is attributed to the fluorination of X in the resulting compound of general formula (2a) by HF deriving from the compound of general formula (1).

Examples of acids other than carboxylic acids include Broensted acids and Lewis acids, of which Lewis acids are preferred to facilitate the reaction. Particularly preferred are metal chlorides, such as aluminum chloride, antimony chloride, ferric chloride, titanium tetrachloride, tin tetrachloride, and zinc chloride, more preferably ferric chloride and zinc chloride. The catalyst may be present in a sufficient amount to exhibit sufficient activity, preferably 0.01 to 50 mole percent, more preferably 5 to 30 mole percent, of the trihalomethyl (pentafluorosulfanylbenzene).

In this step, water is preferably used in an amount of 50 to 200 mole percent of the compound of general formula (1). Water is preferably added slowly, for example, dropwise, because a rapid increase in the concentration of water in the reaction system may deactivate the acid other than carboxylic acids. If water is used, the reaction temperature is preferably 30° C. to 180° C., more preferably 50° C. to 120° C. The specific reaction scheme is as follows:

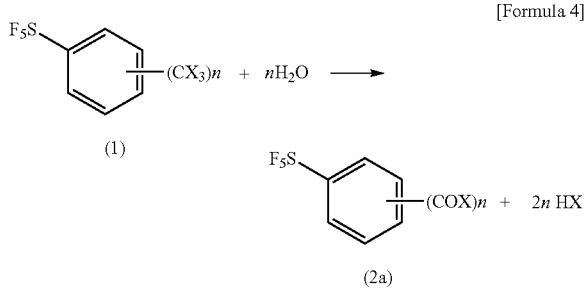

Examples of carboxylic acids usable in this step include acids represented by R″COOH, where R″ is an alkyl group having 1 to 3 carbon atoms or a phenyl group. Particularly preferred carboxylic acids are acetic acid and benzoic acid, which are readily available. Acetic acid is more preferred, which can readily be separated by distillation. The carboxylic acid is preferably used in an amount of 5 to 120 mole percent of the compound of general formula (1). The carboxylic acid is preferably added slowly, for example, dropwise, because a rapid increase in the concentration of the carboxylic acid in the reaction system may produce an acid anhydride as a by-product. If a carboxylic acid is used, the reaction temperature is preferably 50° C. to 140° C. The carboxylic acid also has the advantage of facilitating dissolution of the compound of general formula (1). The specific reaction scheme is as follows:

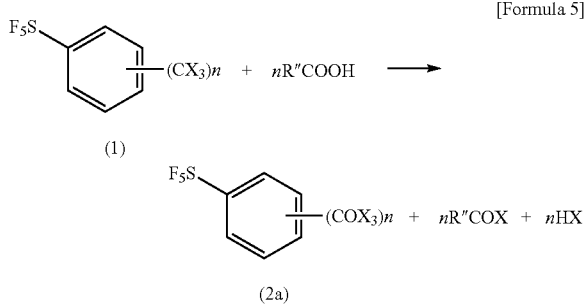

The disiloxane used in this step is represented by general formula (b):

In the formula, R is an alkyl group. For reasons of availability, R is preferably an alkyl group having 1 to 5 carbon atoms, more preferably an alkyl group having 1 to 3 carbon atoms, even more preferably methyl or ethyl. The disiloxane may be used in an amount of 50 mole percent or more of the compound of general formula (1), or may be used in a solvent amount. The disiloxane also has the advantage of dissolving the raw material in the reactor to facilitate the reaction. The reaction scheme is as follows:

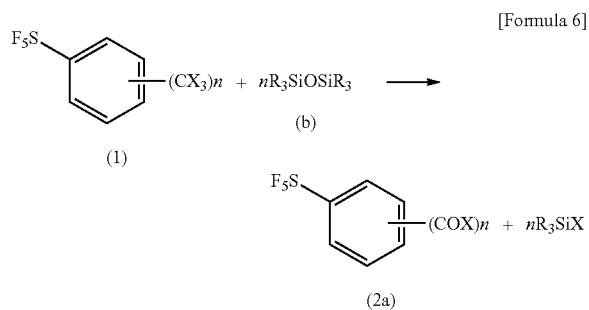

[Formula 6]

This reaction scheme can also be as follows:

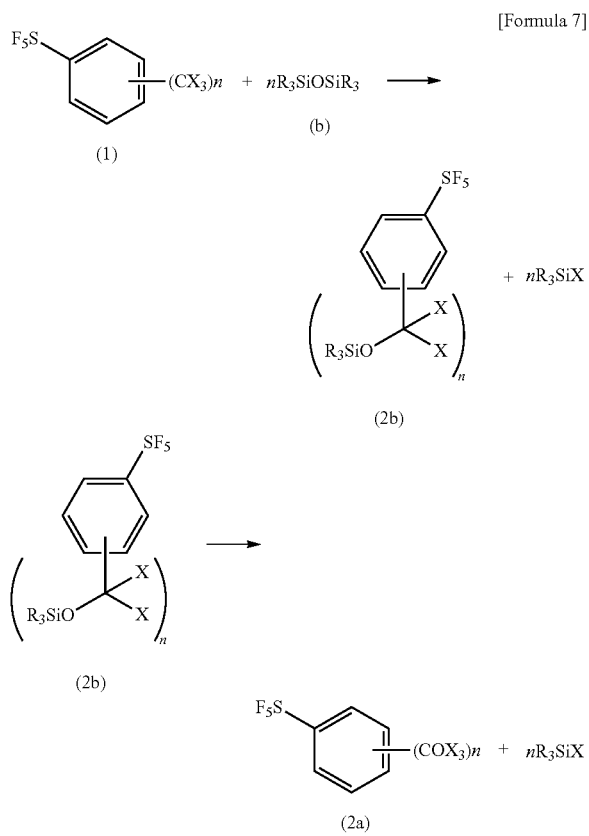

[Formula 7]

That is, if a disiloxane is used, a halide represented by general formula (2b) may be formed in addition to the pentafluorosulfanylbenzoic halide represented by general formula (2a). The halide represented by general formula (2b) is a precursor of the halide represented by general formula (2a). In the formula, X is as defined above, preferably a chlorine atom. R is an alkyl group derived from R in the disiloxane of general formula (b).

In this step, water and a carboxylic acid may be used in combination. Water can convert an acid anhydride, produced as a by-product if a carboxylic acid is used as a reactant, into the target material of the present invention, i.e., a pentafluorosulfanylbenzoic acid. The carboxylic acid facilitates dissolution of the compound of general formula (1), which has poor solubility in water. It is preferred, however, not to use a disiloxane and water in combination. This is because the disiloxane is highly reactive with water and may therefore be deactivated by the following reaction:

$R_3SiOSiR_3 + H_2O \rightarrow 2R_3SiOH$.

Nevertheless, $R_3SiOH$ and $R_3SiX$ formed in this scheme reproduce the disiloxane of general formula (b) through the following reaction:

$R_3SiOH + R_3SiX \rightarrow R_3SiOSiR_3 + HX$.

Thus, a slight amount of water can be present. Specifically, water is preferably present in an amount of 70 mole percent or less, more preferably 50 mole percent or less, of the disiloxane.

The halide formed in step (B1) may be directly subjected to step (B2) without isolation or purification. However, the step of purifying the reaction mixture containing the halide improves the purity of the pentafluorosulfanylbenzoic halide in the reaction mixture, or allows the halide to be isolated from the mixture. Step (B2) through the purifying step yields a purer pentafluorosulfanylbenzoic acid. The purifying step may use distillation or recrystallization, preferably distillation. This is because the halide represented by general formula (2a) has a lower boiling point and can therefore be more readily distilled off than the pentafluorosulfanylbenzoic acid represented by general formula (2). Thus, step (B2) through the purification of the compound of general formula (2a) more efficiently yields a purer pentafluorosulfanylbenzoic acid.

Water and a carboxylic acid, which are significantly reactive, may make it difficult to control the reaction depending on the changes in the amounts of them added and the rates at which they are added. That is, the reaction may proceed past the step of forming the intermediate represented by general formula (2a) to the step of forming the carboxylic acid represented by general formula (2), or may produce an acid anhydride as a by-product. Thus, the use of water and a carboxylic acid enables the pentafluorosulfanylbenzoic acid of general formula (2) to be apparently directly synthesized from the trihalomethyl(pentafluorosulfanylbenzene) of general formula (1). This provides the advantage of readily forming the target compound.

A disiloxane is less reactive than water and a carboxylic acid; therefore, the reaction can be readily terminated after the step of forming the intermediate represented by general formula (2a). Thus, the use of a disiloxane allows the halide intermediate to be readily prepared.

(3) Step (B2)

In this step, the halide of general formula (2a) is converted into a pentafluorosulfanylbenzoic acid. The scheme of this reaction is as follows:

[Formula 8]

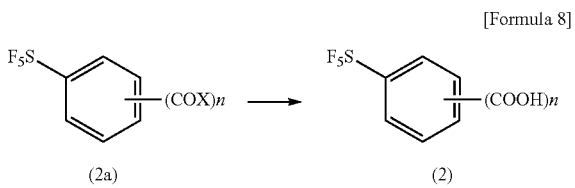

In this step, the halide of general formula (2a) can be hydrolyzed with water to form the target compound of general formula (2). Any overstoichiometric amount, for example, a solvent amount, of water may be added to the pentafluorosulfanylbenzoic halide. The reaction system may have any pH. An alkaline reaction system forms a pentafluorosulfanylbenzoic acid salt. The reaction mixture containing the salt may then be acidified with a Broensted acid to form a pentafluorosulfanylbenzoic acid.

This reaction may use an organic solvent that does not interfere with the reaction in combination. Examples of usable organic solvents include ether solvents, such as diethyl ether and tetrahydrofuran; nitrile solvents, such as acetonitrile; and alcohol solvents, such as methanol and ethanol. The reaction temperature is preferably, but not limited to, 0° C. to 100° C.

If the halide of general formula (2b) is formed in step (B1), the compound can also be converted into a pentafluorosulfanylbenzoic acid in step (B2).

The resulting pentafluorosulfanylbenzoic acid can be isolated or purified by common processes, such as neutralization, extraction, filtration, concentration, distillation, recrystallization, crystallization, sublimation, and column chromatography.

1-2. Second Method of Production

A second method of production includes:

(A) a providing step of providing a trihalomethyl(pentafluorosulfanylbenzene) represented by general formula (1);

(B1) a step of reacting the trihalomethyl(pentafluorosulfanylbenzene) with a disiloxane represented by general formula (b), a carboxylic acid, or water in the presence of an acid other than carboxylic acids to form a pentafluorosulfanylbenzoic halide represented by general formula (2a);

(C1) an esterifying step of reacting the pentafluorosulfanylbenzoic halide with an alcohol to form an ester represented by general formula (2c); and (C2) a step of converting the ester into a pentafluorosulfanylbenzoic acid represented by general formula (2).

Steps (A) and (B1) are as described above. The compound represented by general formula (2b) may be formed in step (B1) of this method of production. The resulting halide is reacted with an alcohol to form an ester represented by general formula (2c) in step (C1).

[Formula 9]

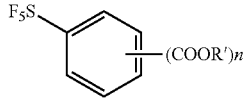

(2c)

In the formula, R' is a linear or branched alkyl group having 1 to 5 carbon atoms, and n is an integer of 1≤n≤3, preferably n=1. The hydrogen atoms on the benzene ring are optionally replaced with a group having an oxygen atom, a group having a nitrogen atom, or a halogen atom.

The alcohol preferably has a linear or branched alkyl group having 1 to 5 carbon atoms. Examples of such alcohols include lower alcohols, such as methanol, ethanol, propanol, butanol, and pentanol. In particular, methanol and ethanol are preferred for ease of handling.

The esterification reaction is preferably performed by reacting the pentafluorosulfanylbenzoic halide with excess alcohol. The resulting ester can be isolated by a purification process such as distillation or recrystallization. In particular, the pentafluorosulfanylbenzoic acid ester can be readily isolated by adding excess alcohol to the halide and distilling the mixture. This process is preferred in that the synthesis and purification of the ester can be simultaneously performed. The resulting ester can then be subjected to step (C2) to yield a purer pentafluorosulfanylbenzoic acid. This method also has the advantage of only requiring a simple apparatus because the compound of general formula (2a), which is highly reactive and corrosive, need not be purified.

Step (C2) may involve hydrolysis of the ester formed in step (C1) with water. The hydrolytic conditions are as described in the first method of production. The scheme of this step is as follows:

[Formula 10]

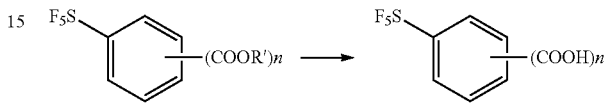

2. Pentafluorosulfanylbenzoic Acid

A pentafluorosulfanylbenzoic acid is a compound represented by general formula (2):

[Formula 11]

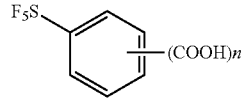

(2)

As described above, X is a halogen atom, and n is an integer of 1≤n≤3. For ease of synthesis, n is preferably 1. The hydrogen atoms on the benzene ring in the formula are optionally replaced with a group having an oxygen atom, a group having a nitrogen atom, or a halogen atom. This compound is useful as an intermediate for drugs and agricultural chemicals.

3. Monotrichloromethyl(pentafluorosulfanylbenzene)

A monotrichloromethyl(pentafluorosulfanylbenzene) is a novel substance represented by formula (5):

[Formula 12]

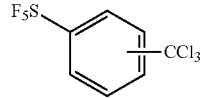

(5)

The hydrogen atoms on the benzene ring are optionally replaced with the group or atom defined above. A monotrichloromethyl(pentafluorosulfanylbenzene) is useful as an intermediate for pentafluorosulfanylbenzoic acids.

Bistrichloromethyl(pentafluorosulfanylbenzene)s and tris-trichloromethyl(pentafluorosulfanylbenzene)s are also novel substances.

EXAMPLES

Example 1

Synthesis of 4-Trichloromethyl(pentafluorosulfanylbenzene)

After a 100 mL flask equipped with a stirrer was purged with $N_2$ gas, 1.4 g (0.10 mol) of $PCl_3$ (from Sigma-Aldrich)

and then 44.1 g (0.20 mol) of 4-methyl(pentafluorosulfanylbenzene) (from UBE America Inc.) were placed into the flask. The mixture in the flask was heated to 130° C. on an oil bath with stirring, and the reaction vessel was irradiated with light from an incandescent lamp (100 W) (from Ace Glass).

The supply of chlorine gas (from Linweld) to the flask was started, and it was stopped after 120 L (5.3 mol) of chlorine gas was supplied. The oil bath temperature was set to 50° C., and 100 g of 2-propanol was gradually added with stirring. After the mixture in the flask was transferred to a 200 mL recovery flask, 50 g of water was added with stirring while the mixture was cooled on an ice bath. White precipitate formed immediately after the addition of water. While the recovery flask was kept on the ice bath, the mixture was stirred for 30 minutes and was then filtered. The residue was washed with 30 g of cool mixture of 2-propanol and water (in a weight ratio of 2:1) to yield a crystalline product. The crystalline product was dried under reduced pressure. The crystalline product was identified as 4-trichloromethyl(pentafluorosulfanylbenzene) by NMR spectroscopy. The amount of product was 42.5 g, and the product yield was 62%.

The results of the NMR spectroscopy (ECX-300 from JEOL Ltd., 300 MHz) are as follows:

$^1$H-NMR (CDCl$_3$): 7.84 (2H, d, J=9 Hz), 8.04 (2H, d, J=9 Hz)

$^{19}$F-NMR (CDCl$_3$): 62.77 (4F, d, J=147 Hz), 82.78 (1F, quin, J=147 Hz)

$^{13}$C-NMR (CDCl$_3$): 95.9 (s), 126.3 (s), 126.4 (t, JCF=5 Hz), 49.2 (quin, JCF=20 Hz), 147.2 (s), 154.8 (quin, JCF=18.7 Hz).

The melting point of the 4-trichloromethyl(pentafluorosulfanylbenzene) was 68.6° C. to 69.4° C. The 4-trichloromethyl(pentafluorosulfanylbenzene) is a novel compound.

Example 2

Synthesis of 4-Pentafluorosulfanylbenzoic Acid (with Disiloxane)

Into a 100 mL flask equipped with a stirrer were placed 40.0 g (111 mmol) of the 4-trichloromethyl(pentafluorosulfanylbenzene) prepared in Example 1, 18.6 g (114 mmol) of hexamethyldisiloxane (from Sigma-Aldrich), and 0.89 g (5 mol %) of FeCl$_3$ (from Sigma-Aldrich). The mixture was heated with stirring at a bath temperature of 70° C. in a N$_2$ atmosphere for 2 days. After the mixture was cooled to room temperature, it was distilled under reduced pressure to yield 24 g of distillate having a boiling point of 87° C. to 94° C. (9 mmHg). The distillate was identified as a mixture of 4-pentafluorosulfanylbenzoic chloride and 4-pentafluorosulfanylbenzoic fluoride (74:24 (areal ratio)) by GC (Agilent 6890 series).

Into a 200 mL flask were placed 8.4 g (210 mmol) of sodium hydroxide, 30 mL of water, and 40 mL of methanol. To the mixture was added 23.7 g of the mixture of pentafluorosulfanylbenzoic halides. After stirring at room temperature overnight, 300 mL of water was added, and the aqueous phase was washed with toluene. To the aqueous phase was added 50 mL of 0.5 M hydrochloric acid, and the organic matter was extracted from the aqueous phase with ethyl acetate. The organic phase (ethyl acetate phase) was washed with water and was then dried over anhydrous sodium sulfate. The organic phase was filtered, and the filtrate was concentrated to yield 22.0 g of white solid of 4-pentafluorosulfanylbenzoic acid (product yield: 80%).

The results of the NMR spectroscopy on the 4-pentafluorosulfanylbenzoic acid are as follows:

$^1$H-NMR (CD$_3$CN): 7.91 (2H, d, J=8.9 Hz), 8.11 (2H, d, J=7.9 Hz), 9.56 (1H, brs, OH)

$^{19}$F-NMR (CD$_3$CN): 61.78 (4F, d, J=147 Hz), 82.83 (1F, quin, 148 Hz).

Example 3

Synthesis of 4-Pentafluorosulfanylbenzoic Acid (with Water)

Into a 50 mL flask equipped with a stirrer were placed 16.08 g (50 mmol) of the 4-trichloromethyl(pentafluorosulfanylbenzene) prepared in Example 1 and 406 mg (5 mol %) of FeCl$_3$. The bath was heated to 70° C. to 75° C., and 900 mg (50 mmol) of water was added dropwise over at least 2 hours. HCl gas was generated during the addition. After the addition was complete, the mixture was heated with stirring for 1 hour. The resulting reaction mixture was transferred to a 200 mL flask, and 100 mL of water was added. The oil bath was heated to 90° C., and the mixture was stirred overnight. After standing to cool, the mixture was filtered, and the solid was washed three times each with 20 mL of water. The residue was transferred to a flask, and 100 mL of 1 M NaOH was added. To the mixture was added 50 mL of toluene, and it was stirred. The aqueous phase was separated and was washed again with 50 mL of toluene. After 20 mL of 6 M HCl was added to the aqueous phase, the precipitate was dissolved in 50 mL of ethyl acetate, and the aqueous phase was separated again. The organic matter was extracted from the aqueous phase with ethyl acetate. The organic phase was washed with saturated brine and was then dried over anhydrous MgSO$_4$. After filtration, the filtrate was concentrated to yield 10.1 g of white solid of 4-pentafluorosulfanylbenzoic acid (product yield: 81%).

Example 4

Synthesis of 4-Pentafluorosulfanylbenzoic Acid (via Ester)

Into a 500 mL flask equipped with a stirrer were placed 105.8 g (329 mmol) of the 4-trichloromethyl(pentafluorosulfanylbenzene) prepared in Example 1, 80.13 g (494 mmol) of hexamethyldisiloxane, and 5.34 g (10 mol %) of FeCl$_3$. The bath was heated to 70° C. to 75° C., and the mixture was heated with stirring for 3 hours. To the reaction mixture was added 5.34 g (10 mol %) of FeCl$_3$, and it was further heated with stirring for 16 hours. The resulting reaction mixture was cooled to room temperature and was mixed with 26 mL of ethyl acetate. Into a 500 mL flask was placed 170 mL of ethanol, and it was cooled on ice. The reaction mixture was added dropwise to the flask. After the addition was complete, the reaction mixture was stirred at room temperature for 1 hour and then with heating under reflux for 2 hours. After the reaction mixture was cooled to room temperature, it was mixed with 106 mL of hexane and was cooled on ice. To the reaction mixture was added 212 mL of water. After thorough stirring, the mixture was separated into different phases. The organic matter was extracted from the aqueous phase with hexane and was washed together with the organic phase with 20% brine. The organic phase was further washed with saturated aqueous sodium bicarbonate solution and was concentrated under reduced pressure. The resulting brown oily product was distilled under reduced pressure to yield 77 g of distillate having a boiling point of 106° C. (6 mmHg). The distillate was identified as ethyl 4-pentafluorosulfanylbenzoate ester by GC (product yield: 85%).

Into a 500 mL flask equipped with a stirrer were placed 76 g (275 mmol) of the ethyl 4-pentafluorosulfanylbenzoate ester, 138 mL of methanol, and 41.2 g (330 mmol) of 45% aqueous potassium hydroxide solution. After stirring at room temperature for 4 hours, the mixture was concentrated under reduced pressure. To the mixture were added 83 mL of water and 83 mL of toluene. After thorough stirring, the mixture was separated into different phases. The aqueous phase was cooled on ice and was mixed with 152 mL of ethyl acetate and 64 mL of 6 M hydrochloric acid. After thorough stirring, the mixture was separated into different phases, and the organic matter was extracted from the aqueous phase with ethyl acetate. The organic matter was washed together with the organic phase with 20% brine and was concentrated under reduced pressure. The resulting concentrate was recrystallized from heptane. The crystalline product was dried under reduced pressure to yield 47 g of white solid of 4-pentafluorosulfanylbenzoic acid (product yield: 81%).

Example 5

Synthesis of 4-Trichloromethyl(pentafluorosulfanylbenzene) (without Catalyst)

After a 100 mL flask equipped with a stirrer was purged with $N_2$ gas, 66.1 g (0.30 mol) of 4-methyl(pentafluorosulfanylbenzene) (from UBE America Inc.) was placed into the flask. The mixture in the flask was heated to 90° C. on an oil bath with stirring, and the reaction vessel was irradiated with light from a mercury lamp (450 W) (from Ace Glass).

The supply of chlorine gas (from Linweld) to the flask was started, and it was stopped after 38 L (1.7 mol) of chlorine gas was supplied over 24 hours. After cooling, 50 mL of methylene chloride was added to the mixture, and it was washed with saturated aqueous sodium carbonate solution and saturated aqueous sodium sulfite solution. The organic phase was concentrated under reduced pressure. The resulting concentrate was recrystallized from a mixture of methanol and water. The crystalline product was dried under reduced pressure to yield 66.7 g of 4-trichloromethyl(pentafluorosulfanylbenzene) (product yield: 68%).

Synthetic Example 1

Synthesis of 4-Pentafluorosulfanylbenzoic Chloride

Into a 100 mL flask equipped with a stirrer were placed 30.0 g (93 mmol) of the 4-trichloromethyl(pentafluorosulfanylbenzene) prepared in Example 1, 16.7 g (103 mmol) of hexamethyldisiloxane, and 0.75 g (5 mol %) of $FeCl_3$. The mixture was heated with stirring at an oil bath temperature of 100° C. in a $N_2$ atmosphere for 2 days. After the mixture was cooled to room temperature, it was distilled under reduced pressure to yield 13.8 g of distillate having a boiling point of 94° C. (6.3 mmHg). The distillate was identified as 4-pentafluorosulfanylbenzoic chloride by GC (product yield: 59%). This reaction probably also formed a chloride represented by formula (2b') (Journal of the Chemical Society, Chemical Communications 1977, 808-809), where $R_3$ is methyl, and X is a chlorine atom.

[Formula 13] (2b')

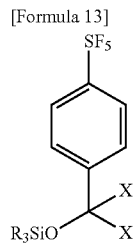

The results of the NMR spectroscopy on the 4-pentafluorosulfanylbenzoic chloride are as follows:

$^1$H-NMR (CDCl$_3$): 7.89 (2H, d, J=8.9 Hz), 8.21 (2H, d, J=8.3 Hz)

$^{19}$F-NMR (CDCl$_3$): 62.16 (4F, d, J=147 Hz), 81.51 (1F, quin, J=150 Hz).

Synthetic Example 2

Synthesis of 4-Pentafluorosulfanylbenzoic Chloride (with Acetic Acid)

Into a 25 mL flask equipped with a stirrer were placed 10.0 g (31.2 mmol) of the 4-trichloromethyl(pentafluorosulfanylbenzene) prepared in Example 1 and 0.15 g (3 mol %) of $FeCl_3$. To the mixture, 1.87 g (31.2 mmol) of acetic acid was added dropwise at an oil bath temperature of 70° C. in a $N_2$ atmosphere for 3 hours. After the addition was complete, the mixture was heated with stirring at an oil bath temperature of 70° C. for 17 hours. After the mixture was cooled to room temperature, it was mixed with 0.49 g (6 mol %) of triphenylphosphine and was stirred for 3 hours. This mixture was distilled under reduced pressure to yield 4.67 g of 4-pentafluorosulfanylbenzoic chloride (product yield: 56%).

Synthetic Example 3

Synthesis of 4-Pentafluorosulfanylbenzoic Chloride (with Water)

Into a 50 mL flask equipped with a stirrer were placed 16.08 g (50 mmol) of 4-trichloromethyl(pentafluorosulfanylbenzene) prepared in Example 1 and 406 mg (5 mol %) of $FeCl_3$. The bath was heated to 70° C. to 75° C., and 900 mg (50 mmol) of water was added dropwise over at least 2 hours. HCl gas was generated during the addition. After the addition was complete, the mixture was heated with stirring for 1 hour. This mixture was distilled under reduced pressure to yield 5.59 g of 4-pentafluorosulfanylbenzoic chloride (product yield: 42%).

The invention claimed is:

1. A method for producing a pentafluorosulfanylbenzoic acid, comprising:

(A) a providing step of providing a trihalomethyl(pentafluorosulfanylbenzene) represented by general formula (1):

[Formula 1] (1)

where X is a halogen atom, n is an integer of 1≤n≤3, and the hydrogen atoms on the benzene ring are optionally replaced with a group having an oxygen atom, a group having a nitrogen atom, or a halogen atom;

(B1) a step of reacting the trihalomethyl(pentafluorosulfanylbenzene) with a carboxylic acid, water, or a disiloxane represented by general formula (b):

$R_3Si—O—SiR_3$ (b)

(where R is an alkyl group)

in the presence of an acid other than carboxylic acids to form a pentafluorosulfanylbenzoic halide represented by general formula (2a):

[Formula 2] (2a)

where X and n are as defined above, and the hydrogen atoms on the benzene ring are optionally replaced with the group or atom defined above; and (B2) a step of converting the pentafluorosulfanylbenzoic halide into a pentafluorosulfanylbenzoic acid represented by general formula (2):

[Formula 3]

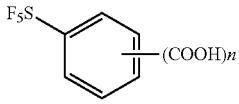
(2)

where n is as defined above, and the hydrogen atoms on the benzene ring are optionally replaced with the group or atom defined above.

2. The method of production according to claim 1, wherein the providing step (A) includes reacting a methyl(pentafluorosulfanylbenzene) represented by general formula (1a):

[Formula 4]

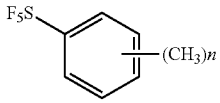
(1a)

where n is an integer of $1 \leq n \leq 3$, and the hydrogen atoms on the benzene ring are optionally replaced with a group having an oxygen atom, a group having a nitrogen atom, or a halogen atom,
with a halogenating agent to form the trihalomethyl(pentafluorosulfanylbenzene) represented by general formula (1).

3. The method of production according to claim 2, wherein the providing step (A) is performed under ultraviolet irradiation.

4. The method of production according claim 1, further comprising a step, prior to step (B2), of purifying a reaction mixture containing the pentafluorosulfanylbenzoic halide formed in step (B1).

5. The method of production according to claim 1, wherein step (B1) includes reacting the trihalomethyl(pentafluorosulfanylbenzene) with a disiloxane represented by general formula (b) in the presence of an acid other than carboxylic acids to form a halide represented by general formula (2b):

[Formula 5]

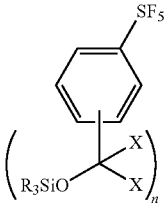
(2b)

where n is an integer of $1 \leq n \leq 3$, X is a halogen atom, R is an alkyl group, and the hydrogen atoms on the benzene ring are optionally replaced with a group having an oxygen atom, a group having a nitrogen atom, or a halogen atom; and
step (B2) includes converting the halides represented by general formulae (2a) and (2b) into a pentafluorosulfanylbenzoic acid represented by general formula (2).

6. A method for producing a pentafluorosulfanylbenzoic acid, comprising:
(A) a providing step of providing a trihalomethyl(pentafluorosulfanylbenzene) represented by general formula (1):

[Formula 6]

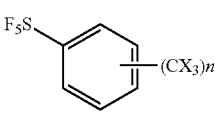
(1)

where X is a halogen atom, n is an integer of $1 \leq n \leq 3$, and the hydrogen atoms on the benzene ring are optionally replaced with a group having an oxygen atom, a group having a nitrogen atom, or a halogen atom;
(B1) a step of reacting the trihalomethyl(pentafluorosulfanylbenzene) with a carboxylic acid, water, or a disiloxane represented by general formula (b):

$R_3Si-O-SiR_3$ (b)

(where R is an alkyl group)
in the presence of an acid other than carboxylic acids to form a pentafluorosulfanylbenzoic halide represented by general formula (2a):

[Formula 7]

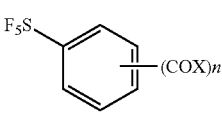
(2a)

where X and n are as defined above, and the hydrogen atoms on the benzene ring are optionally replaced with the group or atom defined above;
(C1) a step of reacting the pentafluorosulfanylbenzoic halide with an alcohol to form an ester represented by general formula (2c):

[Formula 8]

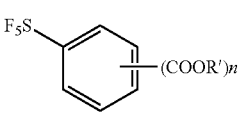
(2c)

where R' is a linear or branched alkyl group having 1 to 5 carbon atoms, n is as defined above, and the hydrogen atoms on the benzene ring are optionally replaced with the group or atom defined above; and
(C2) a step of converting the pentafluorosulfanylbenzoic acid ester into a pentafluorosulfanylbenzoic acid represented by general formula (2):

[Formula 9]

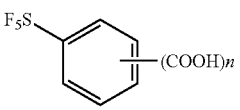
(2)

where n is as defined above, and the hydrogen atoms on the benzene ring are optionally replaced with the group or atom defined above.

7. The method of production according to claim 6, wherein the providing step (A) includes reacting a methyl(pentafluorosulfanylbenzene) represented by general formula (1a):

[Formula 10]

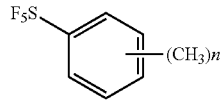
(1a)

where n is an integer of 1≤n≤3, and the hydrogen atoms on the benzene ring are optionally replaced with a group having an oxygen atom, a group having a nitrogen atom, or a halogen atom, with a halogenating agent to form the trihalomethyl(pentafluorosulfanylbenzene) represented by general formula (1).

8. The method of production according to claim 6, wherein the providing step (A) is performed under ultraviolet irradiation.

9. The method of production according to claim 6, wherein step (B1) includes reacting the trihalomethyl(pentafluorosulfanylbenzene) with a disiloxane represented by general formula (b) in the presence of an acid other than carboxylic acids to form a halide represented by general formula (2b):

[Formula 11]

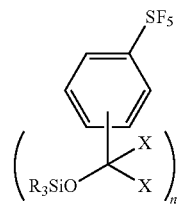
(2b)

where n is an integer of 1≤n≤3, X is a halogen atom, R is an alkyl group, and the hydrogen atoms on the benzene ring are optionally replaced with a group having an oxygen atom, a group having a nitrogen atom, or a halogen atom; and step (C1) includes reacting the halides represented by general formulae (2a) and (2b) with an alcohol to form an ester represented by general formula (2c).

\* \* \* \* \*